United States Patent
Salih et al.

(10) Patent No.: US 12,048,744 B2
(45) Date of Patent: *Jul. 30, 2024

(54) RANKL-SPECIFIC AGENT FOR TREATING METASTATIC DISEASE

(71) Applicant: Probiocon GmbH, Pfeffingen (CH)

(72) Inventors: Helmut Salih, Tübingen (DE); Ludger Grosse-Hovest, Tübingen (DE); Andreas Herrmann, Pfeffingen (CH); Hans-Georg Kopp, Metzingen (DE); Stefanie Maurer, Tübingen (DE)

(73) Assignee: Probiocon GmbH, Pfeffingen (CH)

( * ) Notice: Subject to any disclaimer, the term of this patent is extended or adjusted under 35 U.S.C. 154(b) by 421 days.

This patent is subject to a terminal disclaimer.

(21) Appl. No.: 17/024,425

(22) Filed: Sep. 17, 2020

(65) Prior Publication Data

US 2021/0128722 A1 May 6, 2021

Related U.S. Application Data

(63) Continuation of application No. 15/526,407, filed as application No. PCT/EP2015/076404 on Nov. 12, 2015, now Pat. No. 10,806,786.

(30) Foreign Application Priority Data

Nov. 14, 2014 (EP) ..................... 14193179

(51) Int. Cl.
| | |
|---|---|
| A61K 39/00 | (2006.01) |
| A61K 38/19 | (2006.01) |
| A61K 39/395 | (2006.01) |
| C07K 14/705 | (2006.01) |
| C07K 16/28 | (2006.01) |
| C12Q 1/68 | (2018.01) |
| G01N 33/50 | (2006.01) |
| G01N 33/574 | (2006.01) |

(52) U.S. Cl.
CPC ............ *A61K 39/395* (2013.01); *A61K 38/19* (2013.01); *A61K 38/191* (2013.01); *C07K 14/705* (2013.01); *C07K 14/70578* (2013.01); *C07K 16/2875* (2013.01); *C12Q 1/68* (2013.01); *G01N 33/5011* (2013.01); *G01N 33/574* (2013.01); *C07K 2317/21* (2013.01); *C07K 2317/76* (2013.01); *C07K 2319/30* (2013.01); *G01N 2333/70575* (2013.01)

(58) Field of Classification Search
CPC .. A61K 39/395; A61K 38/191; C07K 14/705; C07K 2317/76; C07K 2319/30; G01N 33/574
See application file for complete search history.

(56) References Cited

PUBLICATIONS

Steger et al (Therap Adv in Med Oncol 3: 233-243, 2011 (Year: 2011).*
Schmiedel et a (Cancer Research 73:683-94, 2012 (Year: 2012).*
Definition of Minimal Residual Disease (Rxlist, published online Apr. 2004) (Year: 2004).*

* cited by examiner

*Primary Examiner* — Lei Yao
(74) *Attorney, Agent, or Firm* — MEDLER FERRO WOODHOUSE & MILLS PLLC

(57) ABSTRACT

The invention provides for a RANKL-specific antagonistic agent recognizing human platelet-expressed receptor activator of nuclear factor kappa-B ligand (pRANKL), for use in treating a cancer patient to prevent or reduce premetastatic lesions in blood.

Figure 1:
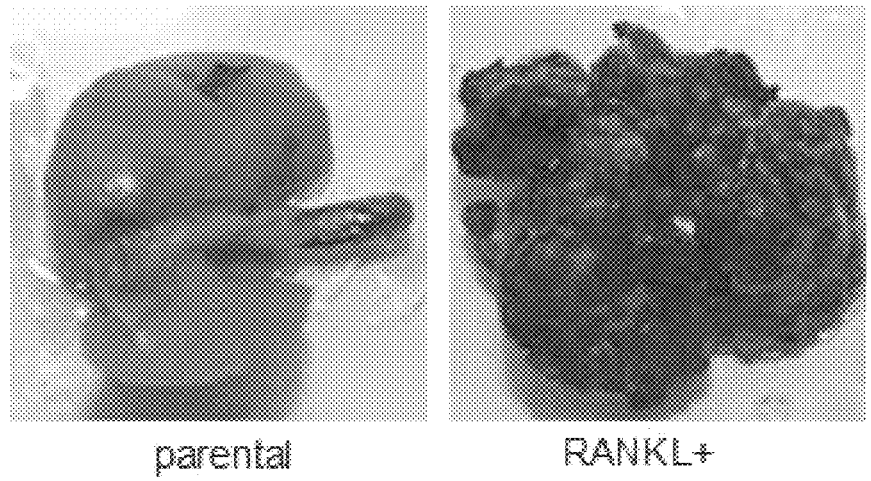

12 Claims, 5 Drawing Sheets
Specification includes a Sequence Listing.

RANK: Q25-P207

Fc-KO: E233P/L234V/L235A/ ΔG236/A327G/A330S

Fig. 6

SEQ ID 1:

EVQLLESGGGLVQPGGSLRLSCAASGFTFSSYAMSWVRQAPGKGLEWVSGITGSGGSTYY
ADSVKGRFTISRDNSKNTLYLQMNSLRAEDTAVYYCAKDPGTTVIMSWFDPWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKS
RWQQGNVFSCSVMHEALHNHYTQKSLSLSPGK

SEQ ID 2:

EIVLTQSPGTLSLSPGERATLSCRASQSVRGRYLAWYQQKPGQAPRLLIYGASSRATGIP
DRFSGSGSGTDFTLTISRLEPEDFAVFYCQQYGSSPRTFGQGTKVEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

SEQ ID 3:

MRRASRDYTKYLRGSEEMGGGPGAPHEGPLHAPPPPAPHQPPAASRSMFVALLGLGLGQVVCSVALFFYF
RAQMDPNRISEDGTHCIYRILRLHENADFQDTTLESQDTKLIPDSCRRIKQAFQGAVQKELQHIVGSQHI
RAEKAMVDGSWLDLAKRSKLEAQPFAHLTINATDIPSGSHKVSLSSWYHDRGWAKISNMTFSNGKLIVNQ
DGFYYLYANICFRHHETSGDLATEYLQLMVYVTKTSIKIPSSHTLMKGGSTKYWSGNSEFHFYSINVGGF
FKLRSGEEISIEVSNPSLLDPDQDATYFGAFKVRDID

Fig. 9
A
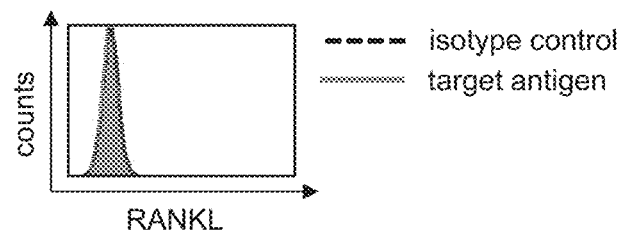
B
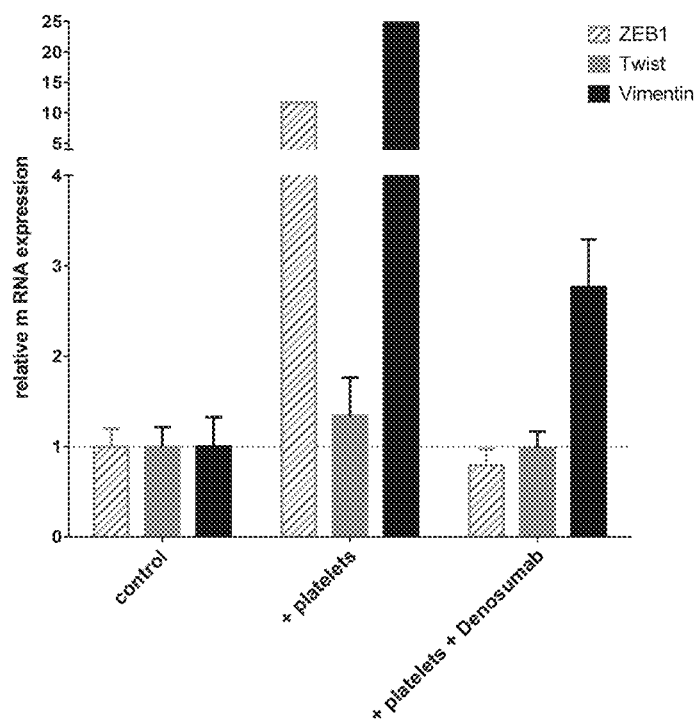

SEQUENCE LISTING

<160> NUMBER OF SEQ ID NOS: 3

<210> SEQ ID NO 1
<211> LENGTH: 452
<212> TYPE: PRT
<213> ORGANISM: Artificial Sequence
<220> FEATURE:
<223> OTHER INFORMATION: heavy chain

<400> SEQUENCE: 1

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145             150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225             230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305             310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385             390                 395                 400

Pro Val Leu Asp Ser Asp Gly Ser Phe Phe Leu Tyr Ser Lys Leu Thr
                405                 410                 415
```

-continued

```
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly Lys
    450

<210> SEQ ID NO 2
<211> LENGTH: 215
<212> TYPE: PRT
<213> ORGANISM: Artificial Sequence
<220> FEATURE:
<223> OTHER INFORMATION: light chain

<400> SEQUENCE: 2

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Arg Gly Arg
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Phe Tyr Cys Gln Gln Tyr Gly Ser Ser Pro
                85                  90                  95
Arg Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 3
<211> LENGTH: 317
<212> TYPE: PRT
<213> ORGANISM: Homo sapiens

<400> SEQUENCE: 3

Met Arg Arg Ala Ser Arg Asp Tyr Thr Lys Tyr Leu Arg Gly Ser Glu
1               5                   10                  15
Glu Met Gly Gly Gly Pro Gly Ala Pro His Glu Gly Pro Leu His Ala
            20                  25                  30
Pro Pro Pro Pro Ala Pro His Gln Pro Pro Ala Ala Ser Arg Ser Met
        35                  40                  45
Phe Val Ala Leu Leu Gly Leu Gly Leu Gly Gln Val Val Cys Ser Val
```

-continued

```
                50                  55                  60
Ala Leu Phe Phe Tyr Phe Arg Ala Gln Met Asp Pro Asn Arg Ile Ser
 65                  70                  75                  80

Glu Asp Gly Thr His Cys Ile Tyr Arg Ile Leu Arg Leu His Glu Asn
                 85                  90                  95

Ala Asp Phe Gln Asp Thr Thr Leu Glu Ser Gln Asp Thr Lys Leu Ile
                100                 105                 110

Pro Asp Ser Cys Arg Arg Ile Lys Gln Ala Phe Gln Gly Ala Val Gln
                115                 120                 125

Lys Glu Leu Gln His Ile Val Gly Ser Gln His Ile Arg Ala Glu Lys
                130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
                180                 185                 190

Trp Ala Lys Ile Ser Asn Met Thr Phe Ser Asn Gly Lys Leu Ile Val
                195                 200                 205

Asn Gln Asp Gly Phe Tyr Tyr Leu Tyr Ala Asn Ile Cys Phe Arg His
                210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
                260                 265                 270

Tyr Ser Ile Asn Val Gly Gly Phe Phe Lys Leu Arg Ser Gly Glu Glu
                275                 280                 285

Ile Ser Ile Glu Val Ser Asn Pro Ser Leu Leu Asp Pro Asp Gln Asp
                290                 295                 300

Ala Thr Tyr Phe Gly Ala Phe Lys Val Arg Asp Ile Asp
305                 310                 315
```

RANKL-SPECIFIC AGENT FOR TREATING METASTATIC DISEASE

TECHNICAL FIELD

The invention refers to a RANKL-specific antagonistic agent which recognizes and optionally neutralizes human platelet-expressed receptor activator of nuclear factor kappa-B ligand (pRANKL), for use in treating a cancer patient, a method for identifying a lead candidate agent, and a method of predicting the metastatic potential in a cancer patient.

BACKGROUND

A large field of research and development focuses on the treatment of cancer. Products under development range from kinase inhibitors, to angiogenesis inhibitors, monoclonal antibodies against tumor targets, apoptosis inducers, antitumor vaccination, and conventional chemotherapeutic agents against various tumor targets and with various cytotoxic effects. Prognosis of cancer patients is mainly determined by the risk of developing metastasis.

During metastasis, host cells are recruited to disseminated tumor cells to form specialized microenvironments ("niches") that promote metastatic progression, but the mechanisms guiding the assembly of these niches are largely unknown. Labelle et al. (PNAS 2014, E3053-3061) describe e.g. that platelet-derived rather than tumor cell-derived signals are required for the rapid recruitment of granulocytes to tumor cells to form "early metastatic niches." Platelets are described to interact with tumor cells during their transit through the circulation thereby forming platelet-tumor cell aggregates and would enhance metastasis via multiple mechanism.

Gay et al. (Nature Reviews 2011, 11:123-134) review the contribution of platelets to tumor metastasis. Among others, within the circulatory system, platelets would guard tumor cells from immune elimination and promote their arrest at the endothelium, supporting the establishment of secondary lesions. The adhesion of platelets to tumor cells and their incorporation into platelet heteroaggregates is described to shield the tumor cells from NK cell activity.

Bone metastases are a frequent complication of many cancers that result in severe disease burden and pain. Regulation of cancer cell migration and bone metastasis by RANK (receptor activator of NF-kB) ligand (RANKL) is described by Jones et al. (Nature 2006, 440:692-696). RANKL triggers migration of human epithelial cancer cells and melanoma cells that express the receptor RANK. RANK is expressed on a series of cancer cell lines and cancer cells in patients. In a mouse model of melanoma metastasis, in vivo neutralization of RANKL by osteoprotegerin results in complete protection from paralysis and a marked reduction in tumor burden in bones, but not in other organs. RANKL produced by bone microenvironment is considered a fertile soil for RANK-positive tumor cells.

Dougall et al. (BoneKEy Reports 2014, 3:519) describes RANKL an essential mediator of osteoclast function and survival, acting through its cognate receptor, RANK. Preclinical data have firmly established that blockade of tumor-induced osteoclastogenesis by RANKL inhibition would not only protect against bone destruction, but would also inhibit the progression of established bone metastases and delay the formation of de novo bone metastases in cancer models. In patients with bone metastases, skeletal complications are driven by increased osteoclastic activity and may result in pathological fractures, spinal cord compression and the need for radiotherapy to the bone or orthopedic surgery (collectively known as skeletal-related events (SREs)). Denosumab, a fully human monoclonal antibody against RANKL, is described to prevent or delay SREs in patients with solid tumors that have metastasized to bone. In addition to its central role in tumor-induced osteolysis, bone destruction and skeletal tumor progression, there is emerging evidence for direct prometastatic effects of RANKL, independent of osteoclasts. For example, RANKL also stimulates metastasis via activity on RANK-expressing cancer cells, resulting in increased invasion and migration.

Tan et al. (Nature 2011, 470 (7335):548-553) describe that fibroblast-recruited, tumor infiltrating CD4+ T cells stimulate mammary cancer metastasis through RANKL-RANK signalling.

Denosumab was approved by the U.S. Food and Drug Administration for use in postmenopausal women with risk of osteoporosis under the trade name Prolia, and as Xgeva, for the prevention of SREs in patients with bone metastases from solid tumors. Clinical trials were investigating Denosumab in giant cell tumors, multiple myeloma with bone metastases, and hypercalcemia of malignancy.

Therapies targeting RANK/RANKL e.g. involve RANKL-specific binders, among them Denosumab, recombinant RANK-Fc (Schmiedel et al. 2013, Cancer Res. 73(2): 683-94), or RANKL-nanobodies (WO2008142164A2). RANKL-binding peptides are described to inhibit bone resorption and/or osteoclast activity (WO2012163887A1).

The effect of Denosumab on bone metastasis in patients with advanced solid tumors is described in a series of documents e.g., Rolfo Christian et al. (Expert Opinion on Biological Therapy, vol. 14, no. 1, 2014, pp 15-26), Scagliotti Giorgio Vittorio et al. (Journal of Thoracic Oncology, vol. 7, no. 12, 2012, pp 1823-1829), Morikawa K. et al. (Database Embase, Elsevier Science publishers, Amsterdam, XP002736136; and Japanese Journal of Lung Cancer, vol. 52, no. 7, 2012, pp 1035-1040), Takeshi Yuasa et al. (Oncotargets and Therapy, vol. 5, 2012, pp 221-229), Hilbe Wolfgang et al. (Magazine of European Medical Oncology, AT, vol. 6, no. 2, 2013, pp 75-82), László Kopper (Pathology & Oncology Research, vol. 18, no. 4, 2012, pp 743-747), Sonya J. Snedecor et al., (Clinical Therapeutics, vol. 34, no. 6, 2012, pp 1334-1349), Sarah Payton (Nature Reviews Urology, vol. 9, no. 1, 2011, pp 1-1), WO 2013/176469 and DATABASE WPI, Thomson Scientific, London, GB, XP002736138; US 2012/114665 A1, and WO 01/08699 A1).

Nakanishi et al. (Platelets 2014, Early Online 1-7) describe the role of platelets to enhance the Th2 response mediated by dendritic cells (DCs) thereby contributing to allergic inflammation. Thrombin receptor agonist peptide (TRAP)-activated platelets were found to express RANKL and induced maturation of myeloid DCs.

B. A. Kerr et al. (Oncogene, vol. 32, no. 36, 2013, pp 4319-4324) describe the role of platelets governing premetastatic tumor communication to bone.

Sharma Deva et al. (Journal of Cellular Physiology, vol. 229, no. 8, 2014, pp 1005-1015) describe the role of platelets in tumor progression. Platelets are described to shield tumor cells from immune host responses and promote tumor cell survival.

Esposito Mark et al. (Pharmacology and Therapeutics, GB, vol. 151, no. 2, pp 222-233) describe targeting tumor stromal interactions in bone metastasis. It is described that circulating tumor cell survival is enhanced by platelet secretion of TGFbeta and formation of platelet aggregates.

SUMMARY OF THE INVENTION

It is the object of the invention to provide for an improved treatment of metastatic disease, and respective anti-metastatic agents.

The object is solved by the subject matter of the invention.

The present invention provides for a RANKL-specific antagonistic agent recognizing human platelet-expressed receptor activator of nuclear factor kappa-B ligand (pRANKL), for use in treating a cancer patient to prevent or reduce premetastatic leasons in blood. Specifically, the medical use comprises the prevention or reduction of premetastatic circulating cell aggregates of platelets with cancer cells. Such aggregates specifically comprise the platelets as activated platelets expressing the pRANKL. Specifically, the RANKL-specific antagonistic agent is used in an effective amount to prevent transduction of signals upon RANK-RANKL interaction that facilitate metastasis upon formation of such premetastatic circulating cell aggregates in blood, or to prevent formation of such premetastatic circulating cell aggregates in blood.

In particular, binding and neutralizing pRANKL would inhibit
a) the dissemination of premetastatic tumor cells,
b) the activation of platelets and/or cancer (or tumor) cells to express pRANKL or to induce RANK-RANKL signaling, thereby inhibiting the transformation of the cells to become prometastatic, and/or
c) the risk of developing haematogeneous spread optionally followed by metastasis formation.

pRANKL specifically turns out to be upregulated when interacting with cancer cells. Therefore, inhibition or neutralizing pRANKL by the agent as described herein, would downmodulate the premetastatic lesion.

The premetastatic lesions are typically involving cells of a precursor lesion, which is characterized by changes in the appearance or nature of the cell before it becomes cancerous, or in the case of a cancer cell before it becomes metastatic.

Therefore, the invention provides for a new method of treatment, wherein a cancer patient is treated with the agent in an effective amount to prevent or reduce premetastatic leasons.

Specifically, the cancer cells originate from RANK-positive cancer cells. The cancer cells can be RANK-positive tumor-forming cancer cells or tumor cells, in particular solid tumor cells, or RANK positive cancer cells which involve the blood and blood-forming organs, e.g. leukemia. Specifically, premetastatic lesions are identified by determining activated platelet-cancer cell aggregates, which are considered circulating premetastatic cell clusters forming niches, thereby promoting cancer metastasis or increasing the risk of developing metastasis, e.g. in distant organs or bone metastasis. Upon interacting with the activated platelets, the cancer cells may be transformed into RANKL positive cancer cells, which are a further characteristic of the premetastatic lesions. Since such platelet-cancer cell aggregates are blood-borne, the metastatic risk or potential is also referred to as blood-borne or haematogeneous.

The agent may specifically recognize and neutralize pRANKL only, or cross-specifically recognizes various forms of RANKL. Specifically, the agent is cross-reactive, recognizing and optionally neutralizing pRANKL and at least one of soluble receptor activator of nuclear factor kappa-B ligand (sRANKL) and membrane-bound activator of nuclear factor kappa-B ligand (mRANKL), or both.

Specifically, the agent is recognizing the RANKL polypeptide, which may comprise the full amino acid sequence of human RANKL (SEQ ID 3), or an epitope in the extracellular portion of the pRANKL, e.g. AA 69-AA 317 of SEQ ID 3), in particular competing with the binding of RANK to RANKL or pRANKL and optionally any other form of RANKL, and thereby substantially inhibiting the RANK-RANKL signalling.

Specifically, the agent binds to pRANKL, thereby inhibiting pRANKL from activating its receptor on cancer cells, e.g. on disseminating or metastasizing tumor cells.

Specifically, the agent is binding to pRANKL monomer, or multimer, such as a multimer of RANKL molecules interacting on the surface of platelets, e.g. wherein one or more pRANKL molecules are bound on the surface of the platelets interacting with each other, and/or interacting with one or more RANKL molecules which are not-platelet bound, or sRANKL. Such multimer may be a dimer, or trimer, or higher multimer, preferably forming a complex with platelet surface-bound pRANKL and/or pRANKL cleaved from the platelet surface, and/or sRANKL, and/or mRANKL. Thus, binding may occur, e.g. on the surface of the platelet, in the microenvironment between a platelet and a cancer cell, or in the circulation upon cleavage of the pRANKL from the platelet surface.

Specifically, metastasis is blood borne, with tumor cell aggregation in distant organs, e.g. any of lung, liver, intestine, skin, muscle, spleen, pancreas, kidney, bone, or brain. Specifically, the risk of developing haematogenic metastatic disease in a patient suffering from a primary solid tumor or cancer of the blood and the lymphatic system, can be effectively reduced.

Specifically, the cancer patient is at risk of or suffering from minimal residual disease and/or recurrence of metastatic disease, optionally wherein the patient has a detectable level of circulating tumor cells in a blood sample, e.g. as determined by the number of disseminated tumor cells in whole blood or a blood fraction thereof, or by specific tumor cell marker. A detectable number of tumor cells is e.g. less than 10, or less than 5, or 4, 3, 2, or 1 circulating tumor cells in a sample of whole blood of at least 5 mL, or 7.5 mL, or 10 mL.

According to a specific embodiment, the patient suffers from a solid tumor selected from the group consisting of epithelial tumors and mesenchymal tumors, or tumors of endodermal, mesodermal and/or ectodermal origin, or a blood-borne cancer, such as leukemia.

Specifically, the patient suffers from breast cancer, pancreatic cancer, gastric cancer, esophageal cancer, renal cell carcinoma, lung carcinoma, colon/rectal/colorectal cancer, melanoma, prostate cancer, head and neck cancer, or leukemia.

According to a specific aspect, the treatment is combined with surgical intervention to remove at least part of a tumor, and/or combined with radiotherapy, and the agent is administered for neoadjuvant or adjuvant therapy. Accordingly, the patient specifically is preparing for or undergoing surgical intervention and/or radiotherapy, or has been treated by a surgical intervention and/or radiotherapy, and is further treated with the agent according to the invention before or after surgery. According to specific examples, such treatment may start between 1 to 30 days before surgery, or during surgery, or within 1 to 30 days after surgery, and the agent may be administered for a continued period, e.g. for 1 to 12 months, or even longer, wherein the agent is administered in regular intervals. Surgical interventions are e.g. therapeutic removal of tumor mass, or biopsy. Surgery is considered a specific risk factor of disseminating tumor cells into the blood stream, thereby provoking platelet-tumor cell aggregate formation. Likewise, radiation therapy can trigger the haematogeneous spread of tumor cells. Therefore, the method of the invention specifically is indicated in combination with surgery and/or radiotherapy which potentially disseminates solid tumor cells.

According to a specific aspect, the agent is administered to the patient in combination with an adjuvant or neoadjuvant combination therapy, preferably chemotherapy, kinase inhibitor therapy and/or immunotherapy. Such combination therapy would specifically target the cancer cell, e.g. any tumor associated antigen, such as selected from the group consisting of epithelial cancer cell marker, soluble factors, or anti-angiogenic therapy.

According to a specific aspect, the agent is selected from the group consisting of antibodies, antibody fragments, receptor-fusion proteins, such as RANK-Fc fusion proteins, peptides, such as inactivated forms of osteoprotegerin, or fragments thereof, small molecules, such as RANK-specific organic small molecules, or aptamers. Exemplary small molecules are small molecule inhibitors of RANKL and TNF, such as described in Coste E, et al. Ann Rheum Dis 2015; 74:220-226. doi:10.1136/annrheumdis-2013-203700. Specific examples are derivatives of butanediol biphenyl-carboxylic acid ester, which are capable of inhibiting RANKL-induced phosphorylation of IκB and extracellular signal-regulated kinase (ERK). For example, compounds where the ester bond is replaced by a ketone may be used, such as ABD328 and ABD345 characterized by the following formula:

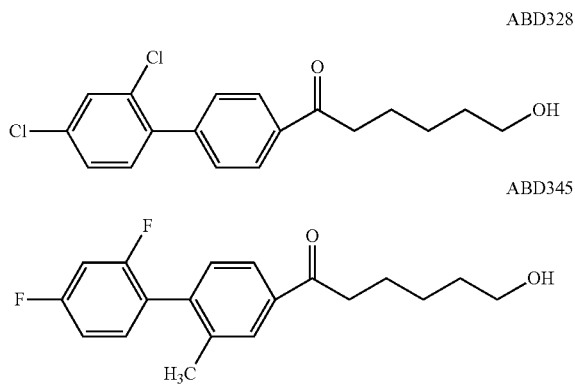

Specifically, the agent is a human or humanized antibody, such as Denosumab, or a functional variant thereof, or an antigen-binding fragment of any of the foregoing, or a RANK-Fc fusion protein. Denosumab (Amgen, Thousand Oaks, CA, USA) is a fully human IgG2 monoclonal antibody specific to RANKL, which is described to suppress bone resorption markers in patients with a variety of metastatic tumors and is being investigated in multiple clinical trials for the prevention and treatment of bone metastases. Chemically, it consists of 2 heavy and 2 light chains. Each light chain consists of 215 amino acids. Each heavy chain consists of 448 amino acids with 4 intramolecular disulfides. The heavy chain amino acid sequence is identified by SEQ ID 1; the light chain amino acid sequence is identified by SEQ ID 2.

Specifically, the agent comprises an Fc antibody fragment, such as a human IgG1 Fc, which is engineered to reduce Fc effector function (e.g. which does not significantly bind to the FcgammaRIIIa, or CD16), and therefore does not exhibit significant antibody-dependent cellular cytotoxicity (ADCC). Exemplary Fc fragments which comprise point mutations to reduce Fc effector function are characterized by at least one of the following mutations: E233P, L234V, L235A, deltaG236, A327G, A330S, wherein nomenclature is according to the EU index of Kabat.

Alternatively, the agent comprises an Fc antibody fragment, such as a human IgG1 Fc, with Fc effector function (e.g. binding to the FcgammaRIIIa, or CD16), such as ADCC. Such agent would have the additional advantage of cell-mediated immune defense whereby an effector cell of the immune system actively destroys the target cell, which is the platelet and/or the cancer cell, preferably the cancer-platelet aggregate.

According to a specific aspect, the agent is administered to the patient in a therapeutically effective amount by systemic administration, preferably by intravenous infusion or bolus injection.

Prior art therapy with Denosumab would typically involve subcutaneous treatment. The present invention would target activated circulating platelets expressing RANKL, or circulating platelet-cancer cell aggregates. Therefore, the intravenous route is specifically preferred.

Preferred doses are, e.g. ranging from 0.5 to 1000 mg, preferably 1-400 mg. If administered subcutaneously, the preferred dosage is ranging from 0.5 to 400 mg.

The invention further provides for a method for identifying a lead candidate agent that is effective in preventing or treating premetastatic lesions, or minimal residual disease and/or recurrence of metastatic disease in a cancer patient, such as a patient preparing for or undergoing surgical intervention to remove at least part of a solid tumor and/or radiotherapy, or who has undergone such surgical intervention and/or radiotherapy, the method comprising screening one or more test agents in a cell-based assay, which assay comprises the steps:
  a) providing a cancer cell culture;
  b) contacting the cell culture with human blood platelets in a reaction mixture with a test agent; and
  c) detecting if the test agent
    i) inhibits RANK signalling by pRANKL; and/or
    ii) decreases the level of platelet binding to the cancer cells;
  thereby identifying a lead candidate agent for preventing or treating premetastatic lesions, and optionally its potential to prevent or treat minimal residual disease and/or recurrence of metastatic disease in a cancer patient.

Specifically, the detection step c) involves testing of both, if the test agent
  i) inhibits RANK signalling by pRANKL; and
  ii) decreases the level of platelet binding to the cancer cells.

Specifically, activated platelets are used in such screening assay, such as thrombin-activated platelets, or those activated by cancer or tumor cells, e.g. activated by RANKL-negative tumor cells, to express pRANKL.

Specifically, the assay is a functional antagonist or neutralizing assay measuring the ability of a putative antagonist (a test agent) to inhibit receptor (RANK) signalling mediated by an agonist (RANKL). For example, a compound can be identified as a RANKL-specific antagonistic agent if the compound substantially inhibits the receptor-mediated signalling.

The invention further provides for a method of predicting the metastatic potential in a cancer patient, comprising
  a) providing a sample of peripheral blood or a platelet containing blood fraction;

b) determining the pRANKL expression in said sample and comparing to a reference value, the differential expression being indicative of premetastatic lesions and an increased potential of developing distant metastases.

For example, the sample or the platelets can be incubated with standard cancer cells with defined metastatic potential, and the level of RANK signalling by the platelet-cancer cell interaction may be determined to obtain a reference value for a specific metastatic potential. Likewise, the platelets can be activated with thrombin and the pRANKL level in the sample may be determined in comparison with a standard.

The pRANKL expression is e.g. determined as the level of pRANKL expression, such as the expression of a nucleotide sequence or the pRANKL polypeptide, or a fragment thereof. The level may be determined qualitatively, but also semi-quantitatively, or quantitatively.

The reference value may be derived from a positive or negative control, or both. The positive control is e.g. representing the level of pRANKL expression of platelets from a cancer patient suffering from metastatic disease conditions. The negative control is e.g. representing the pRANKL expression level of a healthy control subject.

FIGURES

FIG. 1: Lung metastasis model using RANKL transfected melanoma cells. Murine B16-F10 melanoma cells (ATCC), to be identified by black color) that were transfected to express human RANKL (RANKL+) or control cells (parental) were injected in the tail vein of C57BL/6 mice. B16-F10 cells (100,000 cells per mouse). After passing the heart via the blood stream, the malignant cells disseminate to the lungs. The metastatic burden in the lung of the animals was analyzed after 3 weeks, showing drastically increased metastasis upon enhanced RANKL-mediated signalling when RANKL+ cells were used. This is revealed by the higher amount of black coloured areals in the lungs and the destroyed lung architecture.

Figure 2:
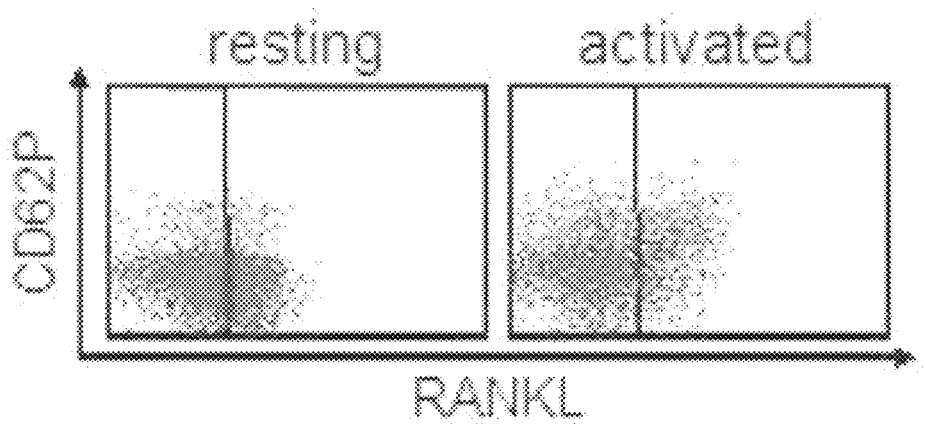

FIG. 2: RANKL expression on resting and activated thrombocytes. Human platelets of healthy donors were isolated by centrifugation of blood samples and then either stimulated with 0.2 U/ml of the classical platelet agonist Thrombin (activated) or left untreated (resting). Platelet surface expression of the activation marker P selectin (CD62P) and RANKL was analyzed by flow cytometry.

Figure 3:
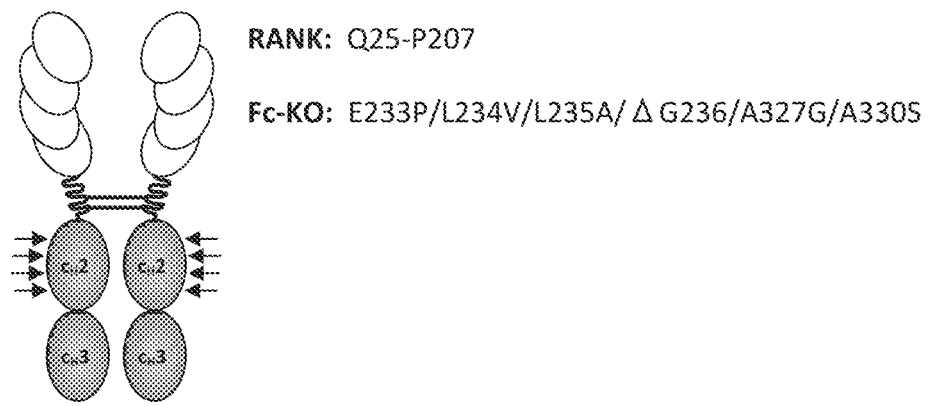

FIG. 3: Structure of RANK-Fc-KO. RANK-Fc-KO fusion proteins consist of the extracellular domain of the human receptor RANK (Q25-P207; Gen Bank Reference NP_0003830) and a human IgG1 Fc part (P217-K447) containing amino acid exchanges E233P/L234V/L235A/ ΔG236/A327G/A330S; Armour et al. 2003, Mol Immunol. 40(9):585-93; Schmiedel et al. 2013) to decrease its affinity and consequently binding to the Fc receptor CD16. Here, all numbering is according to Kabat [EU-Index].

Figure 4:
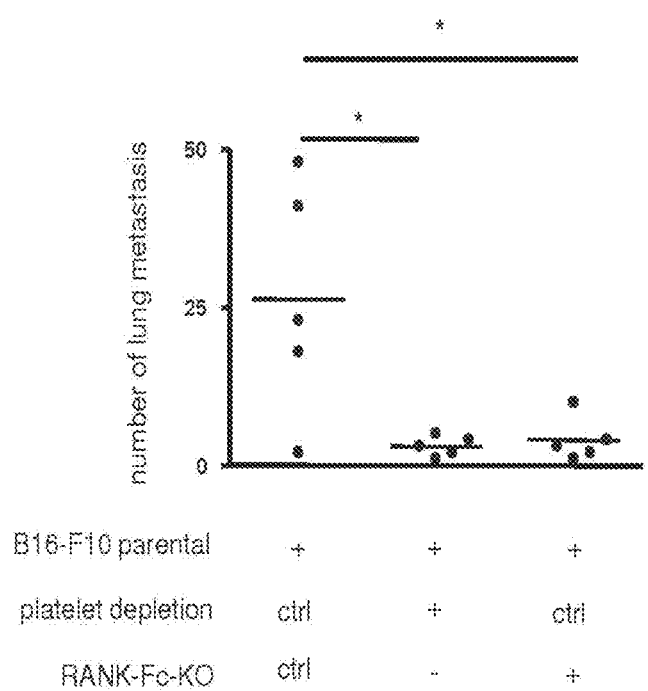

FIG. 4: Lung metastasis model using RANK-Fc-KO. Parental B16-F10 melanoma cells were injected in the tail vein of the indicated numbers of C57BL/6 mice (75,000 per mouse). Additionally, mice in the different groups were treated either with platelet depletion by application of 3 µg/g anti-GPIbα antibody 24 h prior to tumor cell injection, RANK-Fc-KO (100 µg per mouse, on the day of tumor cell injection, repeated two and four days later) as well as appropriate controls (ctrl) as indicated. The number of lung metastasis was counted after sacrifice of mice after 3 weeks.

Figure 5:
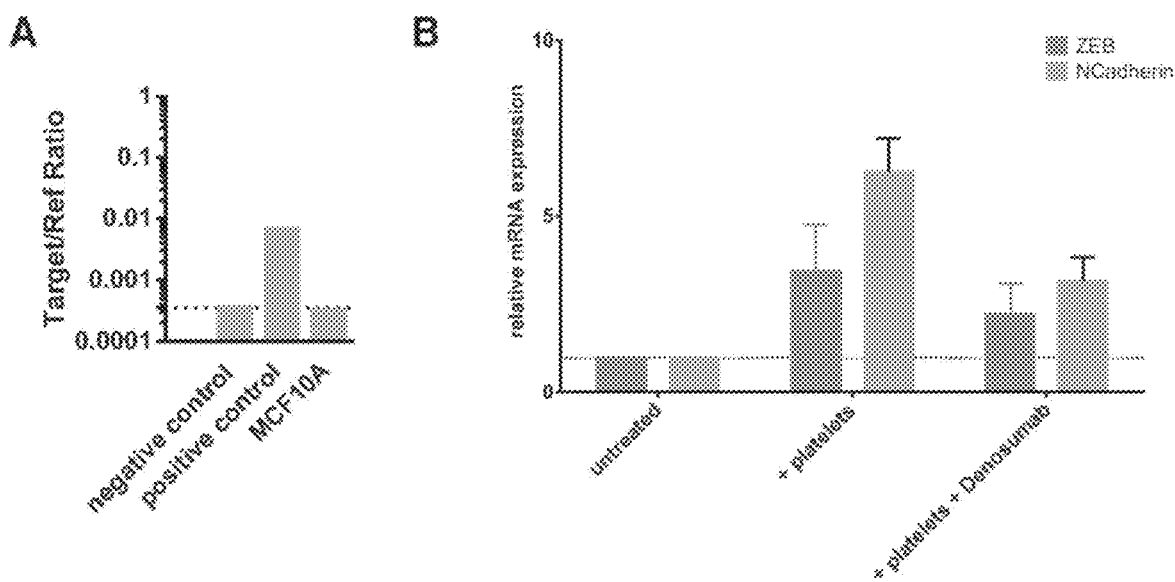

FIG. 5: Prevention of platelet-induced (prometastatic) EMT signaling in immortalized MCF10A cells by RANKL blocking. MCF10A cells (ATCC) as standard model for EMT analysis were studied by quantitiative realtime PCR for (A) RANKL and (B) the markers for mesenchymal phenotype ZEB (Zink finger E-box binding homeobox 1, left column), and NCadherin (right column). To this end, RNA was isolated, reverse transcribed and subjected to SYBR-green based PCR by routine techniques.

(A) The ratio of target (RANKL) to reference (RPL13) gene expression of MCF10A cells and appropriate controls is displayed. The results show no difference between negative control and MCF10A cells thereby excluding that MCF10A cells themselves express RANKL.

(B) Analysis of prometastatic EMT gene signatures in MCF10A cells was performed after 2 days of culture alone (untreated) or with platelets (ratio platelets/tumor cells 5:1) in the presence or absence of the RANKL-neutralizing antibody Denosumab (10 µg/ml). Presence of platelets caused induction of ZEB and NCadherin mRNA expression as markers for prometastatic EMT gene expression that was substantially reduced by the presence of Denosumab.

FIG. 6: Sequences
Denosumab heavy and light chain amino acid sequences:
SEQ ID 1: heavy chain
SEQ ID 2: light chain
Human RANKL amino acid sequence (GenBank: AAB86811.1):
SEQ ID 3: full-length sequence FIG. 7: Neutralisation of RANKL prevents platelet-induced migration of immortalized MCF10A cells. $1*10^5$ MCF10A cells were seeded in the top chamber of a transwell insert (8 µm pore size) either alone (untreated) or with of human platelets ($1.5*10^5$/µl) in the presence or absence of the RANKL-neutralizing antibody Denosumab or the respective isotype control (each 5 µg/ml). After 24 h of incubation, EGF (20 ng/ml) was added to the lower chamber to act as chemoattractant. After a total of 48 h incubation, non-motile cells on the upper side of the membrane were removed while the migrated cells on the lower side were fixed, stained with DAPI and counted under the microscope.

Figure 8:
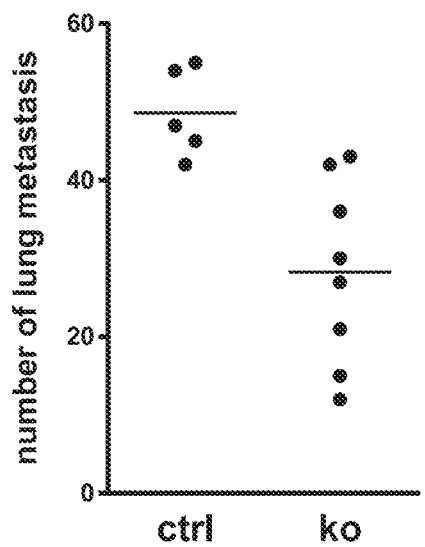

FIG. 8: Lung metastasis model using platelet-specific RANKL knockout mice. B6.129-Tnfsf11$^{tm1.1Caob}$/J mice in which the RANKL gene is flanked by loxP sites (hereinafter referred to as RANKL fl/fl) and C57BL/6-Tg(Pf4-cre) Q3Rsko/J mice which contain a megakaryocte/platetelet specific recombinase (hereinafter referred to as Pf4cre) were obtained both from The Jackson Laboratory (Bar Harbor, ME USA) were bred to generate RANKL fl/fl Pf4 cre/+ knockout (ko) mice in which RANKL is specifically knocked out in megakaryocytes/platelets. For determination of the effects of platelet-expressed RANKL, B16-F10 melanoma cells (75,000 per mouse) were injected via the tail vein in RANKL fl/fl Pf4 cre/+ knockout (ko) mice or C57BL/6 control mice (ctrl) (ko, n=8 animals; ctrl, n=5 animals). The number of lung metastases was counted after sacrifice of mice after 3 weeks.

FIG. 9: Neutralisation of RANKL prevents platelet-induced prometastatic EMT signaling in SK-Mel melanoma cells. (A) SK-Mel (ATCC) cells were analyzed by flow cytometry using anti-RANKL antibody (filled histogram) or the respective isotype control (dotted line) followed by anti-mouse-PE. No difference between isotype control and RANKL-specific antibody-binding was observed, thereby excluding that SK-Mel cells themselves express RANKL.

(B) Analysis of prometastatic EMT gene signatures in SK-Mel melanoma cells was performed after 1 day of culture alone (untreated) or with platelets (ratio platelets/ tumor cells 200:1) or platelets and the RANKL-neutralizing antibody Denosumab (5 μg/ml). Then the markers for mesenchymal phenotype, ZEB (Zink finger E-box binding homeobox 1), Twist and Vimentin were analyzed by quantitiative realtime PCR. To this end, RNA was isolated, reverse transcribed and subjected to SYBR-green based PCR by routine techniques.

Presence of platelets induced prometastatic mRNA expression of all three marker genes that was substantially reduced by the presence of Denosumab.

DETAILED DESCRIPTION OF THE INVENTION

The term "adjuvant" as used herein shall refer to the treatment of cancer during or after a surgical intervention and/or radiotherapy, e.g. for improved therapy.

The term "neoadjuvant" as used herein shall refer to the treatment of cancer prior to a surgical intervention and/or radiotherapy, e.g. for improved therapy.

The term "RANKL-specific antagonistic agent" as used herein shall refer to a compound, which is a RANKL binder substantially neutralizing RANKL, and/or reducing, or inhibiting binding of RANKL to its receptor RANK, thereby antagonizing the RANK-RANKL signalling pathway.

The antagonistic function of the agent is specifically characterized by diminishing, inhibiting, or preventing a cellular response to a receptor (RANK) activated by an agonist (RANKL). Antagonists specifically are competitive antagonists, which can reversibly bind to the RANKL at the same binding site or interfering with the binding site (active site), as the endogenous receptor, without necessarily activating the receptor.

The agent can be any suitable binder or ligand, e.g. selected from the group consisting of small organic or inorganic molecules, carbohydrates, biological macromolecules, peptides, proteins (herein also referred to as polypeptides), peptide analogs, peptidomimetics, antibodies, including antigen-binding fragments of antibodies, nucleic acids, nucleic acid analogs, and a combination of any of the foregoing. In some embodiments, the RANKL-specific antagonistic agent is an immunotherapeutic agent. A specific example of the agent is selected from the group consisting of an antibody, a receptor or osteoprotegerin (which is inactive or rendered inactive, in order to avoid agonistic RANKL binding to its receptor RANK), receptor-fusion protein, e.g. a RANK-Fc fusion protein, a peptide, aptamer, or a small molecule.

Methods for producing and characterizing an antagonistic agent are well-known in the art. In a preferred embodiment, antagonistic binders are produced and screened for predefined properties using one or more cell-based assays. Such assays often involve monitoring the response of cells to a binder, for example cell survival, cell death, change in cellular morphology, or transcriptional activation such as cellular expression of a natural gene or reporter gene.

The production of the recombinant polypeptide antagonistic agent preferably employs an expression system to produce the recombinant polypeptide, e.g. including expression constructs or vectors comprising a nucleotide sequence encoding the polypeptide.

In one embodiment, the antagonistic agent is identified through a drug discovery process, such as including a screen employing combinatorial libraries (random or semi-random) containing potential drug candidates, e.g. peptide libraries, antibody libraries, or chemical compound libraries. Screens may be performed in a high throughput manner using e.g. flow cytometry, and optionally can discriminate between active and non-active or blocked RANK/RANKL interaction. Biological screens may aim at finding novel antagonistic agents specifically targeting pRANKL.

By "substantially reducing or inhibiting" the RANK-RANKL signalling, it is meant that the antagonistic agent (i) inhibits the binding of RANKL to RANK by more than 50%, preferably more than 60%, 70%, 80%, 90% or 95%, or completely inhibits such binding; and/or (ii) functionally inhibits the RANKL-induced pathway, and in particular the signalling following RANK stimulation, e.g. activities of MAPK (Mitogen-Activated Protein Kinase) or SRC-Kinases, or NF-KB signals involved in metastasis formation, e.g. as determined in a lung model as described in the examples section below. Such functional inhibition is e.g. inhibiting metastasis formation by more than about 50%, 60%, 70%, 80%, 90% or 95%, or complete inhibition.

Alternatively, the functional inhibition may be determined ex vivo, e.g. determining the migration of cancer cells via cytoskeletal rearrangements brought on by the activation of Erk1/2 and Src in a standard assay. Specifically, migration and invasion potential of tumor cells may be measured by determining the portion of cells that have passed a porous and/or extracellular-matrix mimicking barrier. Such functional inhibition is e.g. inhibiting migration and/or invasion by more than about 50%, 60%, 70%, 80%, 90% or 95%, or complete inhibition.

The functional inhibition may also be determined by measuring the downregulation of a epithelial-mesenchymal transition (EMT) gene signature, in particular metastasis-associated genes in cancer cells by targeting pRANKL, e.g. by quantitative PCR-based methods, determining any of E-Cadherin, Claudin, SNAIL, or Fibronectin.

The term "antibody" as used herein shall refer to polypeptides or proteins that consist of or comprise antibody domains, which are understood as constant and/or variable domains of the heavy and/or light chains of immunoglobulins, with or without a linker sequence. The antibody as used herein has a specific antigen-binding site to bind the RANKL antigen or one or more epitopes of such antigen, specifically comprising a CDR binding site of a single variable antibody domain, such as VH, VL or VHH, or a binding site of pairs of variable antibody domains, such as a VL/VH pair, an antibody comprising a VL/VH domain pair and constant antibody domains, such as Fab, F(ab'), (Fab)$_2$, scFv, Fv, or a full length antibody.

Specific antibody formats may be used according to the invention, e.g. an antibody comprising or consisting of single variable antibody domain, such as VH, VL or VHH, or combinations of variable and/or constant antibody domains with or without a linking sequence or hinge region, including pairs of variable antibody domains, such as a VL/VH pair, an antibody comprising or consisting of a VL/VH domain pair and constant antibody domains, such as heavy-chain antibodies, Fab, F(ab'), (Fab)$_2$, scFv, Fd, Fv, or a full-length antibody, e.g. of an IgG type (e.g., an IgG1, IgG2, IgG3, or IgG4 subtype), IgA1, IgA2, IgD, IgE, or IgM antibody. The term "full length antibody" can be used to refer to any antibody molecule comprising at least most of the Fc domain and other domains commonly found in a naturally occurring antibody monomer. This phrase is used herein to emphasize that a particular antibody molecule is not an antibody fragment.

The term "antibody" shall specifically include antibodies in the isolated form, which are substantially free of other antibodies directed against different target antigens or comprising a different structural arrangement of antibody domains. Still, an isolated antibody may be comprised in a combination preparation, containing a combination of the isolated antibody, e.g. with at least one other antibody, such as monoclonal antibodies or antibody fragments having different specificities.

The term "antibody" shall apply to antibodies of animal origin, including human species, such as mammalian, such as human or murine, or avian, such as hen, which term shall particularly include recombinant antibodies that are based on a sequence of animal origin, e.g. human sequences.

The term "antibody" further applies to chimeric antibodies with sequences of origin of different species, such as sequences of murine and human origin.

The term "chimeric" as used with respect to an antibody refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "antibody" may further apply to humanized antibodies.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions (FR) in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "antibody" further applies to human antibodies.

The term "human" as used with respect to an antibody, is understood to include antibodies having variable and constant regions derived from human germline immunoglobulin sequences. The human antibody of the invention may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

The term "antibody" specifically applies to antibodies of any class or subclass. Depending on the amino acid sequence of the constant domain of their heavy chains, antibodies can be assigned to the major classes of antibodies IgA, IgD, IgE, IgG, and IgM, and several of these may be further divided into subclasses (isotypes), e.g., IgG1, IgG2, IgG3, IgG4, IgA1, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals, e.g. mammalians including human, that comprises genes or sequences from different origin, e.g. murine, chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

Antibody domains may be of native structure or modified by mutagenesis or derivatisation, e.g. to modify the antigen binding properties or any other property, such as stability or functional properties, such as binding to the Fc receptors FcRn and/or Fcgamma receptor (FCGR). Polypeptide sequences are considered to be antibody domains, if comprising a beta-barrel structure consisting of at least two beta-strands of an antibody domain structure connected by a loop sequence.

It is understood that the term "antibody" also refers to derivatives of an antibody, in particular functionally active derivatives, herein also referred to as functional variants of antibodies. An antibody derivative is understood as any combination of one or more antibody domains or antibodies and/or a fusion protein, in which any domain of the antibody may be fused at any position of one or more other proteins, such as other antibodies, e.g. a binding structure comprising CDR loops, a receptor polypeptide, but also ligands, scaffold proteins, enzymes, toxins and the like. A derivative of the antibody may be obtained by association or binding to other substances by various chemical techniques such as covalent coupling, electrostatic interaction, di-sulfide bonding etc. The other substances bound to the antibody may be lipids, carbohydrates, nucleic acids, organic and inorganic molecules or any combination thereof (e.g. PEG, prodrugs or drugs). In a specific embodiment, the antibody is a derivative comprising a drug, e.g. to obtain an antibody-drug conjugate. Specifically, the antibody may be used together with a tag. Thus, the antibody may be a derivative comprising a tag, such as for analytical or diagnostic purposes, including e.g. for use as in vivo diagnostic. There is not a specific limitation with respect to the usable tag, as far as it has no or tolerable negative impact on the binding of the antibody to its target antigen. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself, e.g. radioisotope labels or fluorescent labels, or, in the case of an enzymatic label, may catalyze chemical alteration of a substrate compound or composition which is detectable.

The term derivative also includes fragments, variants, analogs or homologs of antibodies, e.g. with a specific glycosylation pattern, e.g. produced by glycoengineering, which are functional and may serve as functional variants, e.g. binding to the specific target.

The term "glycoengineered" with respect to antibody sequences shall refer to glycosylation variants having modified immunogenic properties, ADCC and/or CDC as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glycoproteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC). Removal of N-Glycan at N297, e.g. through mutating N297, e.g. to A, or T299 typically results in aglycosylated antibodies with reduced ADCC.

Major differences in antibody glycosylation occur between cell lines, and even minor differences are seen for a given cell line grown under different culture conditions. Expression in bacterial cells typically provides for an aglycosylated antibody.

Antibodies can be devoid of an active Fc moiety, thus, either composed of antibody domains that do not have an FCGR binding site, specifically including any antibody devoid of a chain of CH2 and CH3 domains, or comprising antibody domains lacking Fc effector function, e.g. by modifications to reduce Fc effector functions, in particular to abrogate or reduce ADCC and/or CDC activity. Such modifications may be effected by mutagenesis, e.g. mutations in the FCGR binding site or by derivatives or agents to interfere with ADCC and/or CDC activity of an antibody, so to achieve reduction of Fc effector function or lack of Fc effector function, which is typically understood to refer to Fc effector function of less than 10% of the unmodified (wild-type) antibody, preferably less than 5%, as measured by ADCC and/or CDC activity.

An antibody of the present invention may or may not exhibit Fc effector function. Though the mode of action is mainly mediated by inhibiting the RANKL-RANK signaling in the tumor cell microenvironment, without Fc effector functions, Fc can recruit complement and aid elimination of the target platelet-tumor cell aggregates, from the circulation via formation of immune complexes.

Exemplary antibodies comprise an Fc fragment or at least part of an Fc fragment, such as to maintain the binding site to FcRn, thereby obtaining an antibody with substantive half-life in vivo.

A further example refers to modification of an Fc to obtain reduction of possible ADCC and/or CDC activity, e.g. by a switch of IgG1 to IgG2 subtype or by modifications to reduce binding to the Fc receptor, e.g. by E233P and/or L234V and/or L235A and/or D265G and/or A327Q and/or A330A and/or G236, deletion and/or A327G and/or A330S in a human IgG1 Fc, wherein numbering is according to Kabat [EU-Index].

Further examples refer to a modification to reduce immunogenicity, e.g. by a K.O. glycosylation site, such as N297Q, which provides for an impaired binding to lectin receptor.

An exemplary antibody is Denosumab, or a functional variant or an antigen-binding fragment thereof, e.g. incorporated in the framework of an IgG2 or any other immunoglobulin types or subtypes. For example, the Denosumab antigen-binding site or CDR sequences may be incorporated into an IgG1 antibody, with or without Fc effector function.

It is understood that the term "antibody" also refers to variants of an antibody, including antibodies with functionally active CDR variants of a parent CDR sequence, and functionally active variant antibodies of a parent antibody. For example, functional variants of Denosumab may be engineered and used as further described herein.

Specifically, an antibody variant derived from an antibody of the invention may comprise at least one or more of the CDR regions or CDR variants thereof (of the parent antibody), e.g. at least 3 CDRs of the heavy chain variable region and/or at least 3 CDRs of the light chain variable region, with at least one point mutation in at least one of the CDR or FR regions, or in the constant region of the heavy chain (HC) or light chain (LC), being functionally active, e.g. specifically binding the RANKL antigen.

The term "variant" shall particularly refer to antibodies, such as mutant antibodies or fragments of antibodies, e.g. obtained by mutagenesis methods, in particular to delete, exchange, introduce inserts into a specific antibody amino acid sequence or region or chemically derivatise an amino acid sequence, e.g. in the constant domains to engineer the antibody stability, effector function or half-life, or in the variable domains to improve antigen-binding properties, e.g. by affinity maturation techniques available in the art. Any of the known mutagenesis methods may be employed, including point mutations at desired positions, e.g. obtained by randomization techniques. In some cases positions are chosen randomly, e.g. with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "functionally active variant" of an antibody means a sequence resulting from modification of this sequence (a parent antibody or a parent sequence) by insertion, deletion or substitution of one or more amino acids, or chemical derivatisation of one or more amino acid residues in the amino acid sequence, or nucleotides within the nucleotide sequence, or at either or both of the distal ends of the sequence, e.g. in a CDR sequence the N-terminal and/or C-terminal 1, 2, 3, or 4 amino acids, and/or the centric 1, 2, 3, or 4 amino acids (i.e. in the midst of the CDR sequence), and which modification does not affect, in particular impair, the activity of this sequence. In the case of a binding site having specificity to a selected target antigen, the functionally active variant of an antibody would still have the predetermined binding specificity, or substantially the same biological activity, though this could be changed, e.g. to change the fine specificity to a specific epitope, the affinity, the avidity, the Kon or Koff rate, etc. For example, an affinity matured antibody is specifically understood as a functionally active variant antibody. Hence, the modified CDR sequence in an affinity matured antibody is understood as a functionally active CDR variant.

Preferably, an agent is used which binds to pRANKL with a high affinity, in particular with a high on and/or a low off rate, or a high avidity of binding. The binding affinity is usually characterized in terms of the concentration of the agent, at which half of the binding sites are occupied, known as the dissociation constant (Kd, or KD). Usually a binder is considered a high affinity binder with a $Kd<10^{-8}$ M, preferably a $Kd<10^{-9}$ M, even more preferred is a $Kd<10^{-10}$ M.

Yet, in an alternatively preferred embodiment the individual antigen binding affinities are of medium affinity, e.g. with a Kd of less than $10^{-6}$ M and up to $10^{-8}$ M, e.g. when binding to at least two antigens.

The term "substantially the same biological activity" as used herein refers to the activity as indicated by substantially the same activity being at least 20%, at least 50%, at least 75%, at least 90%, e.g. at least 100%, or at least 125%, or at least 150%, or at least 175%, or e.g. up to 200% of the activity as determined for the comparable or parent antibody.

In a preferred embodiment the functionally active variant of a parent antibody
 a) is a biologically active fragment of the antibody, the fragment comprising at least 50% of the sequence of the molecule, preferably at least 60%, at least 70%, at least 80%, at least 90%, or at least 95% and most preferably at least 97%, 98% or 99%;
 b) is derived from the antibody by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or
 c) consists of the antibody or a functionally active variant thereof and additionally at least one amino acid or nucleotide heterologous to the polypeptide or the nucleotide sequence.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants or analogs.

The term "functionally active variant" also includes naturally occurring allelic variants, as well as mutants or any other non-naturally occurring variants. As is known in the art, an allelic variant is an alternate form of a (poly)peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains or improves a function of the unaltered polypeptide or the nucleotide sequence, when used in combination of the invention. Such sequence alterations can include, but are not limited to, (conservative) substitutions, additions, deletions, mutations and insertions.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).

The "positively" charged amino acids are:
Arginine: (Arg, R) polar, positive; and
Lysine: (Lys, K) polar, positive.

The "negatively" charged amino acids are:
Aspartic acid: (Asp, D) polar, negative; and
Glutamic acid: (Glu, E) polar, negative.

"Percent (%) amino acid sequence identity" with respect to the antibody sequences and homologs described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "antigen" as used herein interchangeably with the terms "target" or "target antigen" shall refer to a whole target molecule or a fragment of such molecule recognized by an agent specifically recognizing the antigen, or capable of specifically binding the target, such as an antibody which recognizes the antigen through binding by the antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site. The term "epitope" as used herein shall in particular refer to a molecular structure which may completely make up a specific binding partner or be part of a specific binding partner to a binding site of an agent as described herein. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding the polypeptide to form a tertiary structure and the amino acids are not necessarily adjacent to one another in the linear sequence.

The antigen as described herein is human RANKL, in particular pRANKL, though the specific binder to pRANKL may cross-specifically recognize sRANKL and/or mRANKL, or be cross-reactive with pRANKL and any of (or both of), sRANKL and mRANKL. The human pRANKL is specifically understood as RANKL originating from human blood platelets (also referred to as thrombocytes), e.g. an antigen expressed on the surface of a human blood platelet, preferably by an activated platelet, which can be targeted with an antagonist that binds thereto. The platelet can also interact with a (RANKL negative) cancer cell to transform such cancer cell into a premetastatic lesion, which itself is capable of expressing RANKL. Thus, the antagonistic agent may as well target the cancer cell expressing RANKL. The pRANKL may be detached or shedded from the surface of the platelet and inhibited by the antagonistic agent as a soluble ligand. pRANKL when expressed on the surface of platelets, may differ from sRANKL in the accessibility of the epitopes. mRANKL may be expressed by tissue, or a cancer cell, and further interacting with a platelet and/or another cancer cell. Further structural differences of pRANKL as compared to other forms of RANKL or compared to RANKL originating form cancer cells and cells of other origin like osteoblasts may be evident upon thorough analysis of the amino acid sequence and glycosylation pattern of pRANKL.

The term "RANKL" includes any variants, isoforms and species homologs of human RANKL which are naturally expressed by cells and which are bound to the surface of cells, e.g. of human blood platelets or tumor cells, or which are present as soluble RANKL in the circulation, as determined in a sample of peripheral blood.

Preferred epitopes of pRANKL are incorporated in the extracellular portion of the RANKL antigen, in particular the extracellular part of the pRANKL or the extracellular part of the transmembrane RANKL, e.g. an epitope which is accessible on the surface of the platelets or cells.

The antagonistic agent as described herein is binding to an epitope of RANKL, which leads to substantial inhibition of the RANKL binding to its receptor RANK, thereby inhibiting the signalling pathway. Since RANKL promotes survival and induces migration of various cancer cells that express RANK, the antagonistic agent as described herein would interfere with the proliferation and metastasis of cancer cells by preventing or reducing premetastatic migration and aggregation of cancer or tumor cells.

The term "metastasis" as described herein shall refer to the spread of malignant tumors to secondary sites, e.g. remote from an original or primary tumor. This normally involves detachment of cancer cells from a primary tumor, entering the body circulation and settling down to grow within normal tissues elsewhere in the body. Such primary tumor is understood as a tumor growing at the site of the cancer origin. Hematopoietic diseases (leukemia, lymphomas and myeloma) are considered disseminated at time of diagnosis. However, also hematopoietic cancer can form metastatic tumors. Although rare, the metastasis of blood and lymphatic system cancers to the lung, heart, central nervous system, and other tissues has been reported. Metastatic tumor cells are understood as cells that have the ability to produce a metastasis or are already a part of a metastatic tumor. Specifically, the primary cancer cells and/or the metastasis as referred to herein is RANK-positive, e.g. as determined by a standard immunohistochemical or a PCR-based method.

Examples of primary mesenchymal tumors are soft tissue tumors, e.g. deriving from muscle, fibrous tissue, and vascular tissue.

Among primary mesodermal and/or ectodermal tumors are melanoma and/or ameloblastoma and primitive neuro-ectodermal tumor of the lung, respectively.

Representative primary, epithelial cell cancers include amongst others breast, prostate, lung, bladder, uterine, ovarian, brain, head and neck, esophageal, pancreatic, gastric, germ cell, and colorectal cancers.

Particular important RANK-positive tumor diseases are breast cancer, pancreatic cancer, gastric cancer, esophageal cancer, renal cell carcinoma, lung carcinoma, colon/rectal/colorectal cancer, melanoma, prostate cancer, head and neck cancer, or other diseases associated with RANK-positive tumor entities.

Among the blood cancers are leukemia, lymphoma, or myeloma.

A patient suffering from leukemia can specifically benefit from the anti-RANKL treatment as described herein, because RANK signaling into leukemic cells may e.g. enhance their proliferative potential and/or alter their resistance to anti-cancer therapeutic intervention e.g. with chemotherapy and/or kinase inhibitors.

Patients treated for cancer and primary tumors often retain a minimal residual disease related to the cancer. That is, even though a patient may have by clinical measures a complete remission of the disease in response to treatment, a small fraction of the cancer cells may remain that have escaped destruction. The type and size of this residual population is an important prognostic factor for the patient's continued treatment.

In certain embodiments, the patient has minimal residual disease after the primary cancer therapy (e.g. chemotherapy, radiation therapy and/or surgery). The antagonistic agent as described herein would be particularly combined with cytoreductive therapy or other therapeutic interventions e.g. immunotherapy, to treat minimal residual disease, and/or as maintenance therapy, e.g. as a prolonged or extended therapy after cessation of another cancer treatment. In addition, the antagonistic agent would delay the re-growth or recurrence of the cancer or tumor, or recurrence of metastasis formation in metastatic disease, e.g. by at least 1 or more months.

Specific metastatic tumor cells are disseminating tumor cells which tend to develop premetastatic tumor cell aggregates in the circulation that trigger metastasis formation in distant organs. It surprisingly tuned out that disseminating RANK-positive tumor cells can aggregate with RANKL-positive platelets in the circulation, such aggregates inducing metastasis formation. Activated platelets can upregulate pRANKL and thereby stimulate RANK on the tumor cells and thus render them premetastatic. Therefore, the cancer patient advantageously treated as described herein suffers from a tumor disease or cancer which mainly metastasizes via the blood vessels, and not or less through the lymphatics.

The platelet-cancer cell aggregates are understood as prometastatic, or a preform of metastases, in particular upon activation of the platelets to express pRANKL. Such preform differs from metastases because the aggregates are present in the circulation, and not yet growing to larger mass as metastases in distant organs. To this point, the prometastatic platelet-cancer cell aggregates are considered an embodiment of a RANK-positive neoplastic disease.

The term "disseminating tumor cells" as used herein primarily refers to tumor cells found in circulation of a patient having a tumor. Though this term typically would not include hematological tumors where the majority of the tumor is found in circulation, the term "Disseminating tumor cell" is as well encompassing (pre)metastatic tumor cells in a patient suffering from blood cancer. Blood cancers may trigger contact of platelets with the cancer cells, optionally resulting in disseminating platelet-cancer cell contact aggregates in the circulation once they are going to metastasize. Blood cancer cells acquire the ability to penetrate the walls of lymphatic or blood vessels, after which they are able to circulate through the bloodstream as circulating (disseminating) tumor cells to other sites and tissues in the body, eventually forming a clinically detectable tumor known as a metastatic or secondary tumor implant. In addition, the pRANKL-RANK signalling may trigger blood cancer disease progression.

The term "prometastatic" as used herein in relation to platelet-cancer cell aggregates is understood in the following way. Cancer or tumor cells and/or platelets can be prometastatic, i.e. promoting metastasis, because of the tendency of aggregating and subsequently binding of the pRANKL-positive platelets to the RANK-positive tumor cell, and initiating the RANK-RANKL signalling. Reciprocal interactions between the cancer cells and the various components of the tumor microenvironment influence tumor progression and metastases although the molecular mechanisms underlying these metastasis-promoting effects are yet ill defined. Identifying and understanding pathways of cancer-platelet or tumor-platelet cross-talk can lead to the development of therapies targeting pRANKL to prevent metastasis at its earliest stage, resulting in improved patient outcome.

"Premetastatic lesions" are herein understood as a precursor lesion, characterized by early cellular and molecular events of cancer dissemination that lead to the creation of a metastasis-promoting microenvironment (pre-metastatic niches). It surprisingly turned out that disseminating tumor cells would cause metastasis upon recruitment of thrombocytes, in particular activated thrombocytes expressing pRANKL. Through interaction with the blood platelets, optionally forming detectable (prometastatic) platelet-cancer cells aggregates, and upon RANK-RANKL signaling in the microenvironment, the cancer cell would become premetastatic, thus change its appearance or nature before it becomes metastatic. Thus, the pRANKL is considered characteristic distinguishing between those cells that are premetastatic lesions or not. The pRANKL is therefore a new target of metastasis prevention or approaches to detect and prevent metastasis at its earliest inception.

By reducing the prometastatic platelet-cancer cell aggregates, the risk of organ-specific metastasis formation is greatly reduced. In particular, this refers to visceral or mesothelial metastasis, or target organs like liver, lung, bone, intestine, skin, muscle, spleen, brain, or kidney, and in many cases target sites other than bones. Visceral metastasis in particular refers to metastases in the viscera, the internal organs of the body, specifically those within the chest such as heart or lungs or the abdomen, such as the liver, pancreas or intestines. Mesothelial metastasis refers to the growth of cancer cells in or at a mesothelium such as the pleura and the peritoneum. In particular, mesothelial metastases can lead to accumulation of fluid in the cavity surrounded by the mesothelium, in particular pleural and/or abdominal effusion, e.g. due to inflammatory reaction and/or increased permeability of the affected mesothelium caused by the metastases.

The term "metastatic potential" as used herein shall refer to the potential for developing minimal residual disease, the recurrence of metastatic disease, the potential for metastatic cancer to progress rapidly, or the potential for metastatic cancer to display resistance to a standard therapy, e.g. chemotherapy and/or immunotherapy.

An increased or high metastatic potential is indicative of a propensity to form distant metastasis or metastasis to multiple sites or organs, or else local, tissue specific, organ-specific, or site-specific metastasis. A high metastatic potential is indicated in a cancer patient, where a relatively high load of disseminated tumor cells are determined in the circulation. In particular, the peripheral blood sample of a cancer patient would contain an increased number of detectable platelets expressing pRANKL, or any of sRANKL or mRANKL, or conglomerates of cancer cells and platelets, as compared to a reference value. Examples for cell lines of high metastatic potential are MDA-MB-231 (mamma carcinoma cell line, derived from metastatic site of patient with Her2/neu positive breast cancer, e.g. available at ATCC (Manassas, Virginia)), or SK-Mel-5 (melanoma cell line, derived from metastatic site of a patient with malignant melanoma, e.g. available at ATCC (Manassas, Virginia)).

In contrast, a low metastatic potential is indicative of a low rate of metastasis or a non-metastatic tumor. The RANK-positive cancer of low metastatic potential would present only with low or limited amount of tumor cells in the circulation. In particular, the peripheral blood sample of a cancer patient would contain only a low or limited number of detectable platelets expressing pRANKL, or pRANKL, or conglomerates of tumor cells and platelets. Examples for cell lines of low metastatic potential are MCF-7 (mamma carcinoma cell line, derived from metastatic site of a patient with Her2/neu positive breast cancer, e.g. available at ATCC (Manassas, Virginia)), or SK-BR-3 (mamma carcinoma cell line, derived from metastatic site of a patient with Her2/neu positive breast cancer, e.g. available at ATCC (Manassas, Virginia)).

Methods of analyzing disseminating tumor cells and assessing their metastatic potential in vivo and in vitro are well-known in the art. Such methods can be improved by the specific determination of pRANKL expression, or by determining the level of premetastatic lesions, in particular prometastatic platelet-cancer cell aggregates in a blood sample, or a platelet containing fraction thereof.

The prognostic assay based on the method of predicting the metastatic potential as further described herein, can be used to determine whether a patient is suitably treated with an agent, e.g. an agonist, antagonist, peptidomimetic, protein, peptide, nucleic acid, small molecule, or other drug candidate to treat cancer or other disorders associated with cancer such as metastatic disease. For example, such assay can be used to determine whether a subject shall be administered with a chemotherapeutic agent.

The term "patient" as used herein shall refer to a warm-blooded mammalian, particularly a human being. In particular the medical use format of the invention or the respective method of treatment applies to a patient in need of prophylaxis or treatment of cancer, tumor or metastatic disease. The patient may be suffering from early stage or late stage disease, or else a patient predisposed of such disease, e.g. by genetic predisposition.

The term "pharmaceutical composition" as described herein shall refer to a composition suitable for administering to a human, i.e. a composition containing components which are pharmaceutically acceptable. Preferably, a pharmaceutical composition comprises an active compound or a salt thereof together with a carrier, diluent or pharmaceutical excipient such as buffer, or tonicity modifier.

The antagonistic agent of the present invention is specifically provided in a pharmaceutical composition. Stable pharmaceutical compositions are contemplated which are prepared for storage. In specific embodiments, the agent having the desired degree of purity is mixed with pharmaceutically acceptable carriers, excipients or stabilizers, and provided as lyophilized formulation, aqueous solution or oil-in-water emulsion. Typically such compositions comprise a pharmaceutically acceptable carrier as known and called for by acceptable pharmaceutical practice, see e.g. Remingtons Pharmaceutical Sciences, 16th edition (1980) Mack Publishing Co. Examples of such carriers include sterilized carriers such as saline, Ringers solution or dextrose solution, optionally buffered with suitable buffers to a pH within a range of 5 to 8.

The formulations to be used for in vivo administration will need to be sterile. This is readily accomplished by filtration through sterile filtration membranes or other suitable methods.

Administration of the pharmaceutical composition comprising the agent for use as described herein is specifically by the systemic route or by parenteral administration, e.g. by the intravenous, intramuscular or subcutaneous route, but also orally, intranasally, intraotically, transdermally, mucosal, topically (e.g., gels, salves, lotions, creams, etc.), intraperitoneally, intramuscularly, intrapulmonary, vaginally, parenterally, rectally or intraocularly. Exemplary formulations as used for parenteral administration include those suitable for intravenous, intramuscular, or subcutaneous injection as, for example, a sterile solution or suspension.

In particular, the intraveneous administration is preferred, e.g. as intraveneous infusion or as a bolus injection. Denosumab is known to be administered by the subcutaneous route. In the new indication of targeting pRANKL, the Denosumab agent would specifically be administered such that it is available in the circulation for a prolonged period of time, thus, the subcutaneous route is specifically less preferred or avoided.

The present invention includes a pharmaceutical preparation, containing as active substance the antagonistic agent in a therapeutically effective amount.

The term "therapeutically effective amount", used herein interchangeably with any of the terms "effective amount" or "sufficient amount" of the antagonistic agent as described herein, is a quantity or activity sufficient to, when administered to the subject effect beneficial or desired results, including clinical results, and, as such, an effective amount or synonym thereof depends upon the context in which it is being applied. In the context of disease, therapeutically effective amounts of the agent may be used to treat, modulate, attenuate, reverse, or affect a disease or condition that benefits from a down-regulation or reduction of premetastatic lesions, platelet-cancer cell aggregates, or prometastatic tumor cell aggregates, e.g. for preventing or treating metastatic disease. An effective amount is intended to mean that amount of a compound that is sufficient to treat, prevent or inhibit such diseases or disorder. The amount of the antagonistic agent that will correspond to such an amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

Moreover, a treatment or prevention regime of a subject (a cancer patient) with a therapeutically effective amount of the antagonistic agent may consist of a single administration, or alternatively comprise a series of applications. For example, the antagonistic agent may be administered at least once a year, at least once a half-year or at least once a month. However, in another embodiment, the antagonistic agent may be administered to the subject from about one time per week to about a daily administration for a given treatment. The length of the treatment period depends on a variety of factors, such as the severity of the disease, the age of the patient, the concentration and the activity of the antagonistic agent. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

A therapeutically effective amount of the antagonistic agent such as provided to a human patient in need thereof may specifically be in the range of 0.5-1000 mg, preferably 1-400 mg, even more preferred up to 300 mg, up to 200 mg, up to 100 mg or up to 10 mg, though higher doses may be indicated e.g. for treating acute disease conditions, such as when preparing for a surgical intervention, or shortly after a surgical intervention, when starting treatment within a 1-7 days following surgery. Subcutaneous doses typically are. ranging within 0.5 and 400 mg.

The term "treatment" as used herein shall always refer to treating patients for prophylactic (i.e. to prevent a disease or disease condition) or therapeutic (i.e. to treat a disease or disease condition) purposes. Treatment of a patient will typically be therapeutic in cases of cancer. However, in case of patients suffering from a primary disease, which are at risk of disease progression or at risk of developing a secondary disease condition or side reaction, e.g. which is dependent on the RANK-RANKL signalling effects, the treatment may be prophylactic. Such treatment for prophylaxis is herein also referred to as treatment or therapy, e.g. employing a therapeutically effective amount.

In one embodiment, the antagonistic agent is the only therapeutically active agent administered to a patient, e.g. as a disease modifying monotherapy.

Alternatively, the antagonistic agent is administered in combination with one or more other therapeutic agents, including but not limited to standard treatment, e.g. chemotherapeutics to treat malignant disease.

In a combination therapy, the antagonistic agent may be administered as a mixture, or concomitantly with one or more other therapeutic regimens, e.g. either before, simultaneously or after concomitant therapy.

The biological properties of the antagonistic agent may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knock-ins and knockouts). Such experimentation may provide meaningful data for determination of the potential of the agent to be used as a therapeutic with the appropriate half-life, effector function, apoptotic activity and IgG inhibitory activity. Any organism, preferably mammals, may be used for testing. For example, because of their genetic similarity to humans, primates, monkeys can be suitable therapeutic models, and thus may be used to test the efficacy, toxicity, pharmacokinetics, pharmacodynamics, half-life, or other property of the agent. Tests of the substances in humans are ultimately required for approval as drugs, and these experiments are contemplated herein. Thus the antagonistic agent of the present invention may be tested in animal models or in humans to determine their therapeutic efficacy, toxicity, immunogenicity, pharmacokinetics, and/or other clinical properties. Denosumab is a commercially available product with well-established biological properties, though the anti-pRANKL effect inhibiting interactions of a cancer cell with thrombocytes turned out to be surprising.

The term "specific" with regard to the RANKL-specific agent as described herein shall refer to a binding reaction which is determinative of the cognate ligand of interest (RANKL) in a heterogeneous population of molecules. Thus, under designated conditions, e.g. immunoassay conditions, the agent that specifically binds to its particular target does not bind in a significant amount to other molecules present in a sample.

A specific binding site or a specific agent is typically recognizing the target only, and not cross-reactive with other targets. Still, the specific binding site may specifically bind to one or more epitopes, isoforms or variants of the target, or be cross-reactive to other related target antigens, e.g., homologs or analogs.

The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The term "surgical intervention" herein also referred to as "surgery" shall refer to a surgical removal, e.g. biopsy, resection or ectomy of tissue comprising all or a part of a tumor, in particular a primary tumor such as a solid tumor and/or one or more metastases.

According to a specific example, the effect of RANKL expression by resting or activated thrombocytes was tested in a lung metastasis mouse model. In the human system it could be shown that activated thrombocytes expressed RANKL at a higher level as compared to non-activated thrombocytes.

According to another example, a RANK-Fc fusion protein was used (Schmiedel et al. 2013, Cancer Res. 73(2):683-94), which is composed of a human RANK receptor and Fc of human IgG1, and which comprises point mutations to reduce its affinity to the Fc receptor FcgammaRIIIa, CD16, which are 233P/L234V/L235A/ΔG236/A327G/A330S (nomenclature according to Kabat, EU index). The effect of the RANK-Fc fusion protein on metastasis formation in a lung metastasis mouse model was determined. It was shown that neutralization of RANKL by the RANK-Fc fusion protein was about as effective as thrombocyte depletion.

Further examples can show that pRANKL is transferred by platelets to RANKL negative tumor cells, thereby transforming the tumor cells to RANKL positive ones. It can also be established that pRANKL induces prometastatic EMT events in tumor cells, and influences migration of tumor cells through the matrigel. In a mouse knockout model conditionally knocking out the RANKL expression in megakaryocytes and platelets, it can be shown that in fact pRANKL induces premetastatic lesions, and pRANKL inhibition would inhibit or reduce metastasis formation.

The foregoing description will be more fully understood with reference to the following examples. Such examples are, however, merely representative of methods of practicing one or more embodiments of the present invention and should not be read as limiting the scope of invention.

EXAMPLES

Example 1: RANKL Expression by RANKL Transfected Melanoma Cells in a Lung Metastasis Mouse Model Mouse melanoma B16-F10 cells which were transfected with human RANKL or the parental cell line were used in a mouse model of lung metastasis. Application of transfected, RANKL-positive, cells resulted in drastically enhanced metastatic burden in the lungs of the animals as compared to the parental cells (control) (FIG. 1). Since it is known that human RANKL can stimulate mouse RANK, these data suggest that increased metastastatic burden in mice which received RANKL-positive tumor cells is due to enhanced RANK signalling into the tumor cells. This is also in line with studies from Jones et al. (2006) which show enhanced metastasis of RANK-positive tumor cells upon para- and/or autocrine stimulation. This experiment proves that providing RANKL for RANK stimulation beyond the levels available under normal circumstances enhances the metastatic potential. The transfection of RANKL therein mimics the contribution/transfer of pRANKL to the tumor cells.

Example 2: pRANKL Expression on Activated Thrombocytes

Since platelets are known to promote tumor metastasis, analysis of potential RANKL surface expression on platelets was performed. While low levels of RANKL could be detected on resting platelets, profound RANKL surface expression was obtained following platelet activation with thrombin (FIG. 2). Thus, activation of platelets, which also occurs upon formation of aggregates with tumor cells, results in rapid upregulation of RANKL expression. The upregulated RANKL is then readily available to interact and stimulate RANK on tumor cells.

Example 3: RANK-Fc Fusion Protein

The immunoreceptor-Fc fusion protein which contains the extracellular fraction of the human receptor RANK and a human immunoglobulin G (hIgG1) was prepared (FIG. 3). The fusion protein displays markedly reduced affinity to the Fc receptor (FcγRIIIa, CD16) due to amino acid exchanges in the IgG1 part which prohibits binding of the Fc part to CD16 under physiological conditions (233P/L234V/L235A/ ΔG236/A327G/A330S, Armour et al., 1999, Schmiedel et al., 2013). This construct, in contrast to Denosumab, displays binding to both, human as well as mouse RANKL and is therefore advantageous for usage in murine models of RANKL neutralisation (Bossen et al. 2006, J Biol Chem 281(2):13964-71, Kostenuik et al. 2009, J Bone Miner Res 24(2):182-95).

Example 4: Effects of RANKL Neutralisation in a Lung Metastasis Model

To examine the role of pRANKL which is expressed upon activation (e.g. after coating of circulating tumor cells in the blood stream) in vivo, the melanoma lung metastasis model was applied. Parental melanoma cells were used to characterize the role of physiologic murine pRANKL in this model. The number of metastasis was drastically reduced upon platelet depletion which is also in line with prior reports. Interestingly, neutralisation of murine RANKL using RANK-Fc-KO fusion proteins resulted in low numbers of metastasis which were comparable to the results obtained upon platelet depletion (FIG. 4). These data point to the fact that metastasis is mediated by pRANKL and that a neutralisation thereof can prevent metastasis formation.

Example 5: Neutralisation of RANKL Prevents Platelet-Induced Prometastatic EMT Signaling in Immortalized MCF10A Cells As a first step we employed quantitative realtime PCR to exclude that MCF10A cells, a classical model for EMT analysis, themselves express RANKL. This served to ascertain that stimulation of tumor-expressed RANK did not occur in an autocrine/paracrine manner independently of platelets. Subsequently MCF10A cells were incubated with human platelets to mimic platelet-coating of tumor cells in the blood as described previously (Kopp et al. 2009, Cancer Res 69(19):7775-83; Placke et al. 2012, Cancer Res 72(2): 440-8; and Placke et al. 2012, 189(1):154-60). Cocultures were additionally performed in the presence or absence of Denosumab to neutralize platelet-derived RANKL. Quantitative real time PCR analysis of the induction of ZEB and NCadherin mRNA demonstrated that presence of platelets induced expression of the two prometastatic genes in MCF10A cells. This was largely reduced by blocking RANKL with Denosumab, thereby providing clear evidence that in fact pRANKL mediates prometastatic effects of platelets on tumor cells upon formation of aggregates and that neutralization of pRANKL can serve to limit the metastatic potential of tumor cells.

Figure 7:
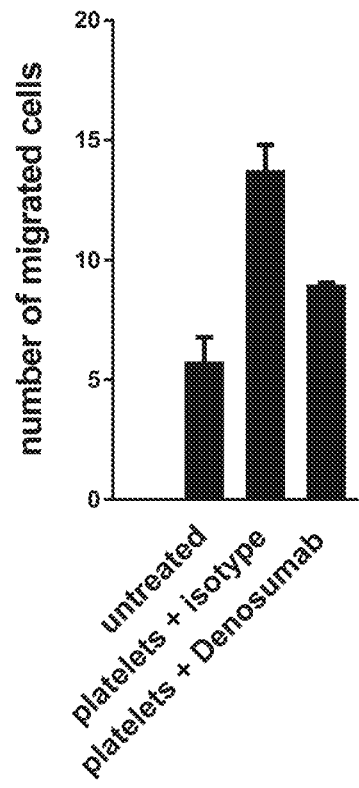

Example 6: Neutralisation of RANKL Prevents Platelet-Induced Migration of Immortalized MCF10A Cells Since the migratory potential of malignant cells is key for their ability to form metastasis, we studied whether platelet-derived RANKL also influenced tumor cell migration. To this end, MCF10A cells were employed in a transwell assay system. MCF10A cells were incubated with human platelets to mimic platelet-coating of tumor cells in the blood as described above in the presence or absence of isotype control or Denosumab in the upper chamber of a transwell system. After 48 h the number of cells that had migrated to the lower chamber along a EGF gradient was determined. We observed that the presence of platelets clearly enhanced the number of migrated cells, and this was largely reduced when platelet-derived RANKL was neutralized by the presence of Denosumab. This demonstrates that pRANKL enhances the migratory potential of malignant cells and thus their prometastatic phenotype upon formation of aggregates and that neutralization of pRANKL can serve to limit the metastatic potential of tumor cells (FIG. 7).

Example 7: Lung Metastasis Model Using Platelet-Specific RANKL Knockout Mice To further examine the role of pRANKL in vivo, the B16-F10 melanoma lung metastasis model was employed. To specifically assess the role of platelet-expressed RANKL, 129-Tnfsf11$^{tm1.1Caob}$/J mice in which RANKL contains flox sites (hereinafter referred to as RANKL fl/fl) and C57BL/6-Tg(Pf4-cre)Q3Rsko/J mice which contain a megakariocte/platetelet specific recombinase (hereinafter referred to as Pf4cre) were bred to generate RANKL fl/fl Pf4 cre/+ knockout (ko) mice in which RANKL is specifically knocked out in megakariocytes/platetels. For determination of the effects of platelet-expressed RANKL, B16-F10 melanoma cells (75,000 per mouse) were injected via the tail vein in RANKL fl/fl Pf4 cre/+ knockout (ko) mice or C57BL/6 control mice (ctrl). The lack of RANKL in platelets resulted in a substantially reduced number of lung metastases in the ko as compared to the ctrl group (FIG. 8). These data further confirm the specific involvement of pRANKL in metastasis formation in vivo, and support our approach that neutralization of pRANKL may serve to prevent metastasis.

Example 8: Neutralisation of RANKL Prevents Platelet-Induced Prometastatic EMT Signaling in SK-Mel Melanoma Cells To confirm and extend the results obtained with immortalized MCF10A cells, we employed the malignant melanoma cell line SK-Mel (ATCC). Flow cytometric analysis excluded that the malignant cells themselves expressed RANKL to ascertain that stimulation of tumor-expressed RANK did not occur in an autocrine/paracrine manner and rather was depedendent on platelets (FIG. 9A). In the experiments shown in FIG. 9B, SK-Mel cells were incubated with human platelets to mimic platelet-coating of tumor cells in the blood as described before. Cocultures were performed in the presence or absence of Denosumab (5 µg/ml) to neutralize platelet-derived RANKL. After 24 h, quantitative real time PCR analysis of the induction of ZEB mRNA demonstrated that, alike with MCF10A cells, presence of platelets induced expression of this prometastatic gene, and this was largely reduced by blocking platelet-derived RANKL with Denosumab. Similar effects were also observed upon analysis of the expression levels of Twist and Vimentin, two further genes involved in metastasis formation/EMT. These analyses confirm and extend our findings obtained with MCF10A cells described in FIG. 5 and provide further evidence that in fact pRANKL mediates prometastatic effects of platelets on tumor cells upon formation of aggregates and that neutralization of pRANKL can serve to limit the metastatic potential of tumor cells.

The invention claimed is:

1. A method of treating a cancer patient suffering from minimal residual disease, the method comprising administering a RANKL-specific antagonistic antibody or antibody fragment recognizing human platelet-expressed receptor activator of nuclear factor kappa-B ligand (pRANKL) in an amount to reduce premetastatic lesions in blood, wherein the antibody or antibody fragment reduces the platelet-association of a cancer cell in the patient.

2. The method according to claim 1, wherein the antibody or antibody fragment is cross-reactive, recognizing pRANKL and at least one of soluble receptor activator of nuclear factor kappa-B ligand (sRANKL) and membrane-bound activator of nuclear factor kappa-B ligand (mRANKL).

3. The method according to claim 1, wherein the antibody or antibody fragment binds to pRANKL, thereby inhibiting pRANKL from activating its receptor on disseminating cancer cells.

4. The method according to claim 1, wherein the antibody or antibody fragment is binding to pRANKL monomer or multimer, preferably forming a complex with platelet surface-bound pRANKL or pRANKL cleaved from the platelet surface.

5. The method according to claim 1, wherein the premetastatic lesions are haematogenous, optionally determined by circulating activated platelet-cancer cell aggregates.

6. The method according to claim 1, wherein the cancer patient is at risk of or suffering from minimal residual disease and/or recurrence of metastatic disease, optionally wherein the patient has a detectable level of circulating tumor cells in a blood sample.

7. The method according to claim 1, wherein the patient suffers from a solid tumor selected from the group consisting of epithelial tumors and mesenchymal tumors, or tumors of endodermal, mesodermal and/or ectodermal origin, or a blood-borne cancer, such as leukemia.

8. The method according to claim 1, wherein the patient suffers from breast cancer, pancreatic cancer, gastric cancer, esophageal cancer, renal cell carcinoma, lung carcinoma, colon/rectal/colorectal cancer, melanoma, prostate cancer, head and neck cancer, or leukemia.

9. The method according to claim 1, wherein the patient is undergoing surgical intervention to remove at least part of a tumor and/or irradiation, and the antibody or antibody fragment is administered for neoadjuvant or adjuvant therapy.

10. The method according to claim 1, wherein the antibody or antibody fragment is a human or humanized antibody, an antigen-binding fragment thereof, or a human or humanized RANK-Fc fusion protein.

11. The method according to claim 1, wherein the antibody or antibody fragment is administered to the patient in a therapeutically effective amount by systemic administration, preferably by intravenous infusion or bolus injection.

12. The method according to claim 1, wherein the antibody or antibody fragment is administered to the patient in combination with an adjuvant or neoadjuvant combination therapy, preferably chemotherapy, therapy with kinase inhibitors and/or immunotherapy.

* * * * *